United States Patent [19]

Buck et al.

[11] Patent Number: 4,947,117

[45] Date of Patent: Aug. 7, 1990

[54] NONDESTRUCTIVE DETECTION OF AN UNDESIRABLE METALLIC PHASE, $T_1$, DURING PROCESSING OF ALUMINUM-LITHIUM ALLOYS

[75] Inventors: Otto Buck, Ames, Iowa; David J. Bracci, Maryland Heights, Mo.; David C. Jiles, Ames, Iowa; Lisa J. H. Brasche, Nevada, Iowa; Jeffrey E. Shield, Ames, Iowa; Leonard S. Chumbley, Ames, Iowa

[73] Assignee: Iowa State University Research Foundation, Ames, Iowa

[21] Appl. No.: 293,120

[22] Filed: Jan. 3, 1989

[51] Int. Cl.⁵ .................. G01N 27/80; G01R 33/12
[52] U.S. Cl. ................................. 324/227; 324/234
[58] Field of Search ............... 324/209, 228, 233–243, 324/226, 227

[56] References Cited

U.S. PATENT DOCUMENTS

| | | |
|---|---|---|
| 3,576,489 | 4/1971 | Law et al. . |
| 3,939,404 | 2/1976 | Tait . |
| 4,078,201 | 3/1978 | Buser .............................. 324/209 X |
| 4,095,180 | 6/1978 | Brown . |
| 4,126,491 | 11/1978 | Karlsson ......................... 324/240 X |
| 4,230,987 | 10/1980 | Mordwinkin . |
| 4,279,163 | 7/1981 | Takekoshi et al. ............. 324/209 X |
| 4,428,782 | 1/1984 | Walker et al. . |
| 4,450,405 | 5/1984 | Howard . |
| 4,481,470 | 11/1984 | Wallace . |
| 4,528,856 | 7/1985 | Junker et al. .................. 324/209 X |
| 4,599,563 | 7/1986 | Tiitto et al. .................... 324/209 X |

OTHER PUBLICATIONS

Review of Progress in Quantitative Non–Destructive Evaluation, by D. J. Bracci, P. Garikepati, D. C. Jiles, and O. Buck, vol. 6B, Thompson and Chimenti, Eds. (Plenum Publishing). Article entitled "NDE Methods for Determination of Thermo–History and Mechanical Properties of Al–Li Alloys", pp. 1395–1402, Jul. 1987.

Review of Progress in Quantitative Non–Destructive Evaluation, by D. J. Bracci, P. Garikepati, D. C. Jiles and O. Buck, vol. 7B, Thompson and Chimenti, Eds. (Plenum Publishing). Article entitled "Search for NDE Methods to Characterize Thermo–History and Mechanical Properties of Al–Li Alloys", pp. 1255–1262, Jul. 1988.

Review of Progress in Quantitative Non–Destructive Evaluation, by L. J. H. Brache, O. Buck, D. C. Jiles, J. D. Snodgrass, and D. C. Bracci, vol. 8, Thompson and Chimenti, Eds. (Plenum Publishing). Article entitled: "Determination of Selected Mechanical Properties of Aged Al–Li Alloys Using NDE Methods".

Primary Examiner—Gerard R. Strecker
Assistant Examiner—Warren S. Edmonds
Attorney, Agent, or Firm—Zarley, McKee, Thomte, Voorhees & Sease

[57] ABSTRACT

A method is disclosed for detecting the $T_1$ phase in aluminum–lithium alloys through simultaneous measurement of conductivity and hardness. In employing eddy current to measure conductivity, when the eddy current decreases with aging of the alloy, while the hardness of the material continues to increase, the presence of the $T_1$ phase may be detected.

8 Claims, 1 Drawing Sheet

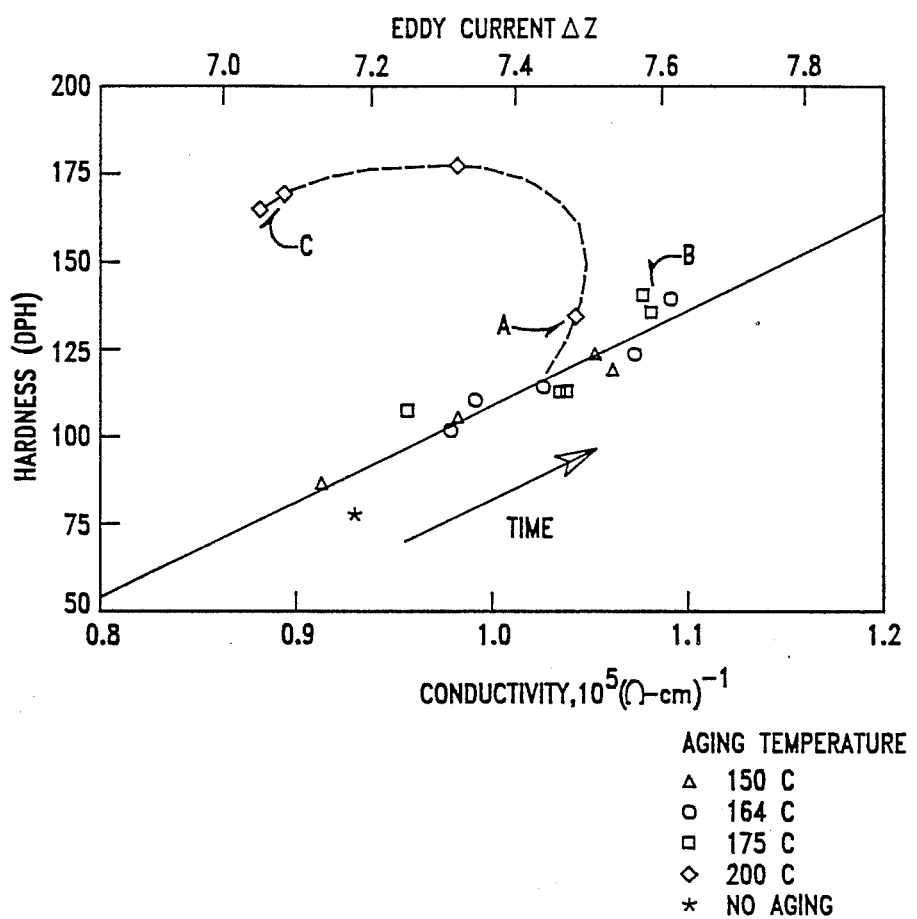

NONDESTRUCTIVE DETECTION OF AN UNDESIRABLE METALLIC PHASE, $T_1$ DURING PROCESSING OF ALUMINUM-LITHIUM ALLOYS

This invention was developed with the assistance of the United States Department of Energy, DOE Case No. BTG-220, and the government may have interest in this invention.

BACKGROUND OF THE INVENTION

Alloys made from aluminum and lithium are very useful since they are lightweight and of high strength. The aerospace industry is especially interested in such alloys because of these features, and their employment in an airframe can reduce the weight of the structure by about 10%.

Precise thermal and thermal-mechanical treatments are required when manufacturing these alloys, however, in order to ensure that the required material properties are obtained. During the precipitation of such alloys, several crystal phases may occur. There is, for example, the aluminum-lithium solid solution phase, and also the metastable cubic stage comprised of $Al_3Li$ having a superlattice structure. The latter cubic phase is highly desirable in that it is through this structure that the alloy gains its strength. The equilibrium phase, $T_1$, on the other hand has a hexagonal structure. The $T_1$ phase can increase the yield strength of the alloys, but has detrimental effects encouraging fatigue crack propagation. It is desired that this phase ($T_1$) be avoided. The typical precipitation sequence for an aluminum-lithium alloy containing between 2% and 5% copper, for example, advances from the solid solution phase to the cubic phase, and further to a cubic phase mixed with the $T_1$ phase.

Strong interest has developed in research on the use of sensors for monitoring the state of the material during processing and in service. In this regard, conductivity measurements and hardness measurements have been found to be particularly sensitive to the changes occurring in the aging of aluminum alloys. See, e.g., L. J. Swartzendruber, W. J. Boettinger, L. K. Ives, S. R. Coriel, and R. Mehrabien, "Nondestructive Evaluation: Microstructural Characterization and Reliability Strategies", O. Buck and S. M. Wolf, eds. TMS-AIME, Warrendale, Pa. 1981, p. 253. Electrical conductivity, in general, increases with aging. These measurements have been used to determine hardness and conductivity of alloys and to monitor condition of the alloy. Computer devices have been developed in order to read eddy current probing of an alloy which is one method of measuring conductivity. E.g., Howard, U.S. Pat. No. 4,450,405. The hardness and the eddy current increase in direct correlation to one another. Thus, researchers to date have used these measurements in order to find the correlating increase in hardness and eddy current profile.

To date, none of these known methods have been found useful in determining the presence of the undesired $T_1$ phase in aluminum-lithium alloys, and there is a need for such a $T_1$ detection system. This invention results from the surprising discovery that the $T_1$ phase may be detected by the dramatic deviation in hardness measurements versus conductivity measurements occurring when that $T_1$ phase is present.

Additionally, detecting such a $T_1$ phase without destruction of the material is especially useful since it can be used on alloys already in use, or for those on the production line.

Accordingly, it is an object of the invention to provide for a method of testing aluminum-lithium alloys to detect the possibility of cracking or similar defects.

It is a further object of the present invention to provide for a method of detecting $T_1$ phase in aluminum-lithium alloys.

It is another object of this invention to provide for a method of detecting $T_1$ phase in aluminum-lithium alloys that does not destroy the alloy.

A further object of the invention is to provide for a convenient and inexpensive method of detecting $T_1$ phase in aluminum-lithium alloys.

Yet another object of the invention is to provide for a method of detecting $T_1$ phase in aluminum-lithium alloys that may be used on alloys during production or when such alloys are in use.

SUMMARY OF THE INVENTION

The invention relates to a method of detecting $T_1$ phase in aluminum-lithium alloys. It employs simultaneous measurement of the conductivity and hardness of the material, and determination of deviations between the conductivity measurements and hardness measurements. Once $T_1$ phase is present in the alloys, the electrical conductivity will decrease rather than increase with aging of the alloy, while at the same time, the hardness will continue to increase even in the presence of the $T_1$ phase. This unusual deviation in the measurements occurs only if $T_1$ phase is present and thus determines the presence of $T_1$ phase.

BRIEF DESCRIPTION OF THE DRAWING

FIG. 1 is an illustrative plot of hardness versus DC conductivity and eddy current impedance response for one aluminum-lithium alloy tested.

DETAILED DESCRIPTION OF THE INVENTION

The method of this invention may be applied to aluminum-lithium alloys. The addition of lithium provides desired properties, with aluminum making up the predominant part of the alloy. In a binary aluminum-lithium alloy, the lithium amount cannot exceed its solid solubility limit in aluminum which is about 3.6 wt. % at 600° C.

Most often, lithium is added to an alloy in amounts up to 2.5 wt. %. Where amounts over this are used, the likelihood of the $T_1$ phase occurring is very high.

The alloys may contain any of a variety of additions. Copper is often incorporated at 2 to 5 wt. %. Small amounts of various other additions such as zirconium, silicon, iron, manganese and cadmium, among others can be included. Examples of formulations include the Alcoa 2090 alloy composed of 2.7 wt. % copper, 2.2 wt. % lithium, 0.12 wt. % zirconium, 0.08 wt. % silicon, 0.12 wt. % iron, and the remaining amount aluminum. Another Alcoa alloy, designated 2020 contains 4.5 wt. % copper, 1.1 wt. % lithium, 0.5 wt. % manganese, 0.2% cadmium, and the remaining amount aluminum. Other examples include Alcoa alloys 2014, 2024 and 2219, discussed at W. D. Rummel, *Materials Evaluation* June 1966, 24, 322-326; M. Rosen, E. Horowitz, L. S. Swart and Weber, S. Fick, R. Mehrabian, *Material Science and Engineering*, 1982, 53, 191, 198; and R. A. Chihoski, *Metal Progress*. May 1983, 127, 27-32, incorporated herein by reference.

Since the alloys are precipitation hardened, precise heat treating is necessary to produce optimum properties. In order to achieve these, such alloys are produced through three steps to precipitation harden the alloy; including solution heat treating, quenching, and aging. During solution heat treatment, an alloy is heated from a multi-phase region to a single-phase region. This produces the strengthening precipitates that form during aging. During quenching, or rapid cooling, the dissolved elements from the second phase stay in solid solution uniformly throughout the matrix, and this is referred to as the metastable state. Cooling the material quickly avoids precipitation of the second phase which could produce loss of strength. Aging then follows, and typically small, coherent metastable strengthening precipitates form homogeneously and uniformly throughout the material. Examples of aging include natural aging at room temperature, or artificial aging at elevated temperatures.

Conductivity is directly related to the material's ultimate strength. E.g., W. D. Rummel, *Materials Evaluation, supra*. It may be measured in a number of ways and any of a variety of known methods of measuring conductivity may be employed. Examples of methods which may be used include measurement by eddy current, which produces an electrical current induced by alternating magnetic field, or using the Van der Pauw method which is a four point technique that gives results independent of the location and nature of the electrical contact. L. J. Van der Pauw *Philips Technical Review*, 1958-59, 20, 220-224. The eddy current is the preferred method since it is a contact free technique.

There are many known methods of measuring hardness, such as use of a standard Vickers (diamond pyramid hardness-DPH) indenter. It is possible that ultrasonic contact impedance measurements may be feasible in that they produce microscopically small indentations which do not require corrective machining.

Both conductivity and hardness normally increase with increased aging of aluminum-lithium alloys. An empirical correlation between eddy current and hardness indicates a linear relationship with the correlation coefficient of R equal to 0.99. This is because the alloying additions in the solution in the solid phase are very effective in scattering the conduction electrons. As precipitation occurs, the resistivity per solute atom decreases which in turn increases the conductivity. At the same time, the hardness increases due to precipitation hardening, at least up to peak hardness conditions.

It is a surprising discovery here that there is a strong deviation from the general rule that conductivity increases with aging in samples in which the $T_1$ phase has been found. Instead, when $T_1$ phase is present, the measurements deviate; conductivity drops while hardness increases. Thus, it has been discovered that when hardness and conductivity are measured, and the hardness does not correlate to the conductivity, the presence of the $T_1$ phase may be detected.

It is essential to measure both conductivity (directly, or via eddy current measurements, for example) and hardness. If there is a deviation in the normal relationship between these measurements, then the $T_1$ phase is present. It is not necessary to contrast these measurements with measurements of other alloys since it is only the deviation in relationship between the measurements which must be detected.

A standard to be applied is created by measuring the hardness and conductivity of samples of the alloy which are at different states of aging, and finding the normal hardness and conductivity correlating increase associated with increased aging. Then measurements of conductivity and hardness of the alloy to be tested are taken and compared to the norm.

While not wishing to be bound by any theory, it is believed, as the data below show, that the loss in conductivity occurring when the $T_1$ phase is present is caused by severe lattice strains accompanying $T_1$ phase. At the same time, long, thin plate-like precipitates forming in the $T_1$ phase may contribute to the increased hardness.

The following is presented by way of example and is not intended to limit the invention.

EXAMPLE I

Three samples were prepared from aluminum-lithium alloy 2090 provided by Alcoa. The numerical reference refers to the 2,000 series, as described in "Metals Handbook", provided by the American Society of Metals, Vol. 2, Nonferrous Alloys. The 2,000 series alloys generally have 2-4% copper. The basic material employed had a nominal composition of 2.7% by weight copper, 2.2% lithium, 0.12% zirconium, 0.08% silicon, and 0.12% iron. Cooling rates after solid solution treatment at 540° C. were 130° C./second and 2° C./second respectively.

The three samples were identified as A, B, and C. Aging treatments were carried out between 150° C. and 200° C. in argon with aging times of up to 33 hours. Sample A was aged at 200° C. for three hours, sample B aged at 175° C. for 33 hours, and sample C aged at 200° C. for 33 hours.

The microhardness measurements were performed on a Tukon hardness machine using a diamond indenter of square pyramidal shape with an opening angle of 136° C. and a 3,000 g load. A Nortec NDT 15 eddy scope with a 5 kHz probe was used for the eddy current measurements. Both the resistive and reactive parts of the complex impedance were determined using digital volt meters. The total change in impedance, $\Delta Z$, was calculated by using the formula $\Delta Z^2 = (\Delta R^2 + \Delta^2)^{\frac{1}{2}}$. DC conductivity was measured using a stable DC current supply in conjunction with a high sensitivity nanovoltmeter. The DC conductivity is given as the inverse of the resistivity.

FIG. 1 shows the results of the eddy current and hardness response, as well as showing DC conductivity. Sample A and Sample B follow the expected increase with aging correlation between hardness and eddy current. Sample C, however, deviated from this. While hardness continued to be high, eddy current decreased dramatically, indicating presence of $T_1$ phase.

The samples were then subjected to Transmission Electron Microscopy in order to determine the morphology and crystal structures of the phases present in the samples. Thin foils were obtained by double-jet electro polishing in a solution of 25% nitric acid and 75% methanol at $-25°$ C. and 20 V. The samples were examined using a JEOL 100 CX operating at 120 kV.

Selected area diffraction patterns of sample A reveal only the precipitation of the metastable crystal phase which grows with a cube/cube orientation with respect to the matrix. The results showed a large coherency with a matrix producing little lattice strain, as was evidenced by the lack of strain contrast in bright field micrographs. Dark field microscopy reveals a fine dispersion of the spherical metastable phase particles. In sample B, which was aged for a longer time but at a lower temperature, microstructure very similar to that of sample A is present. However, a greater amount of the cubic phase has formed resulting in more intense precipitate reflections in the selected area diffraction. Thus, in both samples A and B, only the cubic phase occurs in large enough volume fraction as to cause discernable diffraction patterns.

A quite different microstructure was found to exist for sample C. Selected area diffraction patterns showed two precipitate phases; the cubic phase, as was seen in samples A and B, and the newly formed $T_1$. The existence of the $T_1$ phase severely strains the lattice. The morphology of the cubic phase was similar to that of the previous samples. Rod-like $\theta$ precipitates are noted in all three samples, where $\theta$ is similar to that appearing in Al-Cu alloys. R. J. Rioja and E. A. Ludwiczak, "Aluminum-Lithium Alloys III", C. Baker, P. J. Gregson, S. J. Harris and C. J. Peel eds., The Institute of Metals, London, 1986.

These results confirm that the unusual decrease in the eddy current response, observed after aging at 200° C. for 33 hours, is caused by the severe lattice strains accompanying the $T_1$ phase, and increased hardness likely occurs in relation to the rod-like precipitates.

Thus, it can be seen that there is a direct correlation between the variation for the normal increase in eddy current response accompanying aging, while hardness continues to increase, and the presence of the $T_1$ phase. The confirmed relationship exists in many tested samples, indicating a reliable detection system.

EXAMPLE II

1. Prepare ten coupons (20 mm×20 mm×5 mm) of the Al-Li-Cu alloy. Anneal the coupons for 0.5 hours at 540 C. followed by an ice water quench. Retain one of these specimens and age the remaining nine at 150 C., 164 C. or 175 C. for 3 h, 6 h or 33 h respectively.

2. Determine for all ten specimens the total change of impedance, $\Delta Z$, using a low frequency eddy current probe. $\Delta Z$ is found as the difference between impedance when the probe is nulled in air and when it is in contact with the sample.

3. Determine for all ten specimens the diamond pyramid hardness.

4. Determine the calibration curve of the DPH versus $\Delta Z$ curve for this set of specimens which will not contain the $T_1$ phase. A linear dependence of the form $$DPH = a(\Delta Z) + b$$

is expected, with the coefficients a and b to be determined using a linear least square analysis of the experimental results. Note that the coefficients will depend on the eddy current probe used and will only be valid for that probe.

5. Determine the 95% confidence band of the linear correlation. This confidence band represents +/− two standard deviations.

6. Determine the $\Delta Z$ and DPH on the specimens with unknown thermal history. A deviation of the obtained $\Delta Z$-DPH value by more than two standard deviations from the linear correlation indicates the presence of the $T_1$ phase.

It can be seen, therefore, that the invention accomplishes at least all of its objectives.

What is claimed is:

1. A nondestructive method of detecting undesirable metallic $T_1$ phase in aluminum-lithium alloys comprising:
   measuring hardness and conductivity of multiple reference samples of an alloy each of said multiple reference samples at different degrees of aging from one another;
   determining the correlating increase of hardness and conductivity of said multiple reference samples associated with increased degree of aging of said samples;
   measuring hardness and conductivity of an alloy to be tested; and
   using said measurements of hardness and conductivity of multiple reference samples as a standard of correlation between increasing hardness and conductivity measurements associated with increased aging and detecting whether said hardness measurements or said conductivity measurements of said alloy tested deviated from the standard in order to detect the presence of $T_1$ phase.

2. The method of claim 1 wherein said conductivity is measured by producing an electrical current induced by an alternating magnetic field and measuring conductivity of said current.

3. The method of claim 1 wherein said $T_1$ phase is determined when said conductivity measurements of said alloy tested deviate from the conductivity measurements of samples tested and said hardness measurements of said alloy tested do not deviate from the hardness measurements of said samples tested.

4. The method of claim 1 wherein said aluminum-lithium alloy also contains copper.

5. A method of detecting the presence of undesirable metallic $T_1$ phase in aluminum-lithium alloys comprising:
   measuring hardness of multiple reference samples of an alloy each of said multiple reference samples at different degrees of aging from one another;
   measuring conductivity of said multiple reference samples of an alloy each of said multiple reference samples of different states of aging from one another;
   determining the linear relationship of said hardness and conductivity measurements of said multiple reference samples to the degree of aging of said samples;
   measuring hardness of an alloy to be tested;
   measuring conductivity of said alloy to be tested; and
   comparing said hardness measurements and said conductivity measurements of said alloy tested to detect any deviation in measurements of said alloy tested from said linear relationship of the measurements of said samples.

6. The method of claim 5 wherein said linear relationship is determined by determining linear correlation of the hardness versus conductivity curve for said samples.

7. The method of claim 6 wherein said deviation is determined by observing a variation of two standard deviations from said linear correlation.

8. The method of claim 5 wherein said conductivity measurements are made by producing an electrical current induced by an alternating magnetic field and measuring conductivity of said current.

* * * * *